United States Patent [19]

Condon

[11] 4,311,840
[45] Jan. 19, 1982

[54] 2,3,6,7-TETRAHYDRO-2-THIOXO-4H-OXAZOLO[3,2-a]-1,3,5 TRIAZIN-4-ONES

[75] Inventor: Michael E. Condon, Lawrenceville, N.J.

[73] Assignee: E. R. Squibb & Sons, Inc., Princeton, N.J.

[21] Appl. No.: 206,340

[22] Filed: Nov. 13, 1980

[51] Int. Cl.³ .................................................. C07D 251/00
[52] U.S. Cl. ...................................... 544/223; 424/249
[58] Field of Search ............................................ 544/223

[56] References Cited

U.S. PATENT DOCUMENTS

| | | | |
|---|---|---|---|
| 3,455,920 | 7/1969 | Yale | 542/289 |
| 3,463,778 | 8/1969 | Yale | 542/287 |
| 3,609,148 | 9/1971 | Hoegerle | 544/223 |
| 3,719,676 | 3/1973 | Crank | 544/223 |
| 3,979,381 | 9/1976 | Rovnyak et al. | 542/449 |
| 3,984,549 | 10/1976 | Bochis | 544/223 |
| 3,994,880 | 11/1976 | Krapcho et al. | 542/450 |

OTHER PUBLICATIONS

Wittekind, et al., J. Org. Chem. 26, 444 (1961).
K. D. Kampe, Liebigs Ann. Chem. 752, 142 (1971).
K. D. Kampe, Liebigs Ann. Chem. 593 (1974).
Poos, et al., J. Med. Chem. 6, 266 (1963).
Capuano, et al., Chem. Ber. 104, 3039–3047 (1971).

*Primary Examiner*—Ethel G. Love
*Attorney, Agent, or Firm*—Lawrence S. Levinson; Burton Rodney

[57] ABSTRACT

A compound of the formula wherein
$R_1$ is phenyl or substituted phenyl when $R_2$ is hydrogen or lower alkyl; and
$R_2$ is phenyl or substituted phenyl when $R_1$ is hydrogen or lower alkyl.

These compounds are useful as anti-inflammatory agents.

8 Claims, No Drawings

2,3,6,7-TETRAHYDRO-2-THIOXO-4H-OXAZOLO[3,2-A]-1,3,5 TRIAZIN-4-ONES

BACKGROUND OF THE INVENTION

Krapcho, et al. in U.S. Pat. No. 3,994,880 disclose anti-inflammatory compounds of the formula

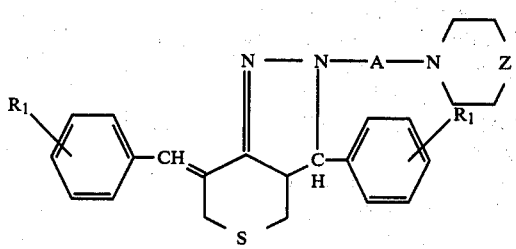

Rovnyak in U.S. Pat. No. 3,979,381 discloses anti-inflammatory compounds of the formula

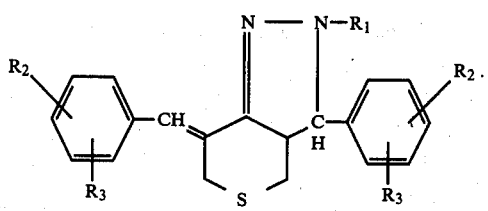

SUMMARY OF THE INVENTION

This invention provides new compounds of the formula

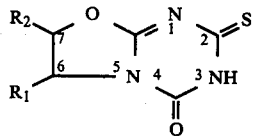

wherein
$R_1$ is phenyl or substituted phenyl, when $R_2$ is hydrogen or lower alkyl; and
$R_2$ is phenyl or substituted phenyl when $R_1$ is hydrogen or lower alkyl. The foregoing symbols have the same meaning throughout the specification.
$R_1$ and $R_2$ may have either a cis or trans relationship.

The compounds of Formula I are useful as anti-inflammatory agents and as such may be used in the treatment of chronic inflammatory diseases such as rheumatoid arthritis. Also, the Formula I compounds are useful in treating leukemia.

DETAILED DESCRIPTION OF THE INVENTION

The invention in its broadest aspects relates to derivatives of the compounds of formula I above.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The $C_1-C_4$ members and especially the $C_1$ and $C_2$ members, are preferred.

The term substituted phenyl represents a phenyl group wherein at least one hydrogen has been replaced by a halogen, lower alkyl, phenyl lower alkyl, lower alkoxy, phenyl lower alkoxy, lower alkylthio, phenyl lower alkylthio or halo substituted lower alkyl.

The term phenyl lower alkyl includes a phenyl ring attached to a lower alkyl group as defined above. Phenylmethyl and phenylethyl are preferred.

The halogens are chlorine, bromine and fluorine; chlorine and fluorine being preferred.

The term halo substituted lower alkyl represents a lower alkyl group wherein at least one hydrogen has been replaced by a halogen.

The term lower alkoxy represents a lower alkyl group as defined above, bonded through an oxygen and the term lower alkylthio represents a lower alkyl group as defined above bonded through a sulfur.

The compounds of formula (I) are prepared by reacting 4,5-dihydro-2-oxazolamines of the formula

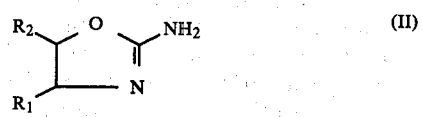

with ethoxycarbonyl isothiocyanate. $R_1$ and $R_2$ are as defined above.

The compounds of formula II are prepared by treatment of amino-alcohols of the formula

(wherein $R_1$ and $R_2$ are as defined above) with cyanogen bromide. The procedure of this treatment is described by G. I. Poos et al., J. Med. Chem. 6 266 (1963); (see Example 2).

The stereochemical relationship between $R_1$ and $R_2$ in the compounds of formula II is determined by that of the compounds of formula III i.e, erythro aminoalcohols yield 4,5-dihydro-2-oxazolamines having $R_1$ and $R_2$ cis, while threo amino-alcohols yield compounds of formula II in which $R_1$ and $R_2$ are trans.

An alternative method of preparing compounds of formula II is by heating in a solvent such as water, halo-ureas of the formula

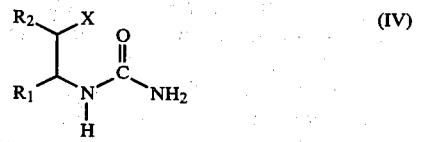

wherein $R_1$ and $R_2$ are as defined above, and wherein X is chlorine, bromine or iodine. The procedural details for this method have been described by R. R. Wittekind, et al., J. Org. Chem. 26, 444 (1961); K. D. Kampe, Liebigs Ann. Chem., 593 (1974); (See Example 1).

The stereochemical relationship between $R_1$ and $R_2$ in the compounds of formula (II) is determined by that of the compounds of formula (IV), i.e., halo-ureas having the erythro configuration yield 4,5-dihydro-2-oxazolamines having $R_1$ and $R_2$ trans, while those having a threo configuration yield formula II compounds in which $R_1$ and $R_2$ are cis.

Compounds of formula IV can be made by procedures known in the art such as described by Wittekind, et al., J. Org. Chem. 26, 444 (1961); K. - D. Kampe, Liebigs Ann. Chem., 752 142 (1971); and K.- D. Kampe, Liebigs Ann. Chem., 593 (1974).

Preferred compounds of formula I are those wherein $R_1$ or $R_2$ is substituted phenyl.

Most preferably $R_1$ or $R_2$ is halo substituted phenyl, the most preferred halo substituent being fluorine.

The compounds of Formula I, are useful in treating inflammation in mammalian species, e.g., guinea pigs. Joint tenderness and stiffness (in conditions such as rheumatoid arthritis) are relieved by the above described compounds.

The compounds of this invention can be formulated for use as antiinflammatory agents according to accepted pharmaceutical practice in oral dosage forms such as tablets, capsules, elixirs, or powders, or in an injectable form in a sterile aqueous vehicle prepared according to conventional pharmaceutical practice. The compounds of this invention may be administered in amounts of 100 mg/70kg/day to 2 g/70kg/day, preferably 100 mg/70 kg/day, to 1 g/70kg/day.

The compounds of Formula I are useful in treating leukemia in mammalian species, e.g. mice. Mice inoculated with strain p388 leukemia cells were after a growth period treated with a formula I compound. The Formula I compound decreased the number of leukemia cells.

The following examples are specific embodiments of the invention. Temperatures in the following examples are in degrees centigrade (°C).

EXAMPLE 1

6-(4-Fluorophenyl)-2,3,6,7-tetrahydro-2-thioxo-4H-oxazolo[3,2-a]1,3,5-triazin-4-one (a) 4-(4-Fluorophenyl)-4,5-dihydro-2-oxazolamine A solution of 24.4 g (0.2 mole) of p-fluorostyrene in 400 ml of ether is treated with 40 g of powdered silver cyanate and cooled in an ice bath. While stirring vigorously, 50.8 g (0.2 mole) of iodine is added in one portion. Stirring is continued for one hour cold and two hours at room temperature. The salts are removed by filtration and washed well with ether. The filtrate (800 ml) is cooled in an ice bath and ammonia is bubbled through the solution for 1 hr. The near white solid which precipitates is harvested and washed with ether, yielding 41.5 g.

This is added to 2 liters of water and the mixture is heated under reflux for 3 hrs. The hot solution is poured through a glass wool plug to remove a small amount of insoluble material. After cooling, the filtrate is made basic with aqueous sodium hydroxide. The product is extracted into chloroform, dried and freed of solvent in vacuo leaving 19.6 g (54%) of white solid. Ether is added and 13.0 g (36%) of crystalline material is harvested. A 6.5 g sample of this is recrystallized twice from ethyl acetate-isopropyl ether to give 4-(4-fluorophenyl)-4,5-dihydro-2-oxazolamine 1.9 g, mp 116°–121°.

Anal. Calcd. for $C_9H_9N_2OF$: C, 59.99%; H, 5.03%; N, 15.55%; F, 10.54%; Found: C, 59.90%; H, 5.24%; N, 15.38%; F, 10.81%.

(b) 6-(4-Fluorophenyl)-2,3,6,7-tetrahydro-2-thioxo-4H-oxazolo[3,2,a]1,3,5-triazin-4one A solution of 6.5 g (36.1 mmol) of 4-(4-fluorophenyl)-4,5-dihydro-2-oxazolamine in 60 ml chloroform is treated dropwise (10 min) with 10 mlethoxycarbonylisothiocyanate, cooling when the reaction mixture became warm. After stirring at room temperature for 1.5 hr., the precipitated near white solid (7.4 g, 77%) is harvested. This was recrystallized from 1 liter of methanol to give 6-(4-fluorophenyl)-2,3,6,7-tetrahydro-2-thioxo-4H-oxazolo[3,2-a]1,3,5-triazin- 4-one 5.64 g (59%), mp 211°–217°.

Anal. Calcd. for $C_{11}H_8N_3O_2SF$: C, 49.81%; H, 3.04%; N, 15.84%; S, 12.08% F, 7.16%; Found: C, 49.89%; H, 2.80%; N, 16.06%; S, 12.02%; F, 7.12%.

EXAMPLE 2

2,3,6,7-Tetrahydro-7-phenyl-2-thioxo-4H-oxazolo-[3,2-a]-1,3,5-triazin-4-one (a) 5-Phenyl-4,5-dihydro-2-oxazolamine A solution of 15.5 g (0.146 mole) of cyanogen bromide in 50 ml of methanol is added over 15 minutes to a stirred solution of 20.0 g (0.146 mol) of 60-aminomethylbenzyl alcohol and 24.0 g (0.292 mol) of sodium acetate in 300 ml of methanol at 0°–5°, and the resulting mixture is stirred at 0°–5° C. for 45 minutes. The methanol is then removed in vacuo, the residue diluted with water, and concentrated aqueous potassium carbonate is added. The resulting solid is filtered off, washed with water, dried in vacuo and recrystallized from benzene yielding 5-phenyl-4,5-dihydro-2-oxazolamine m.p. 135°–136° C.

(b) 2,3,6,7-Tetrahydro-7-phenyl-2-thioxo-4H-oxazolo-[3,2-a]-1,3,5-triazin-4-one

By following the procedure of Example 1 (b) but substituting 5-phenyl-4,5-dihydro-2-oxazolamine in place of 4-(4-fluorophenyl)-4,5-dihydro-2-oxazolamine then 2,3,6,7-tetrahydro-7-phenyl-2-thioxo-4H-oxazolo[3,2-a]-1,3,5-triazin-4-one is formed.

EXAMPLE 3

(cis)-2,3,6,7-Tetrahydro-6-methyl-7-phenyl-2-thioxo-4H-oxazolo[3,2-a ]-1,3,5-triazin-4-one (a) cis 4-methyl-5-phenyl-4,5-dihydro-2-oxazolamine By following the procedure of Example 2 (a) but substituting erythro amino-alcohol dl-norephedrine for α-aminomethyl benzyl alcohol yields cis-4-methyl-5-phenyl-4,5-dihydro-2-oxazolamine.

(b) (cis)-2,3-6,7-Tetrahydro-6-methyl-7-phenyl-2-thioxo-4H-oxazolo[3,2-a]-1,3,5-triazin-4-one By following the procedure of Example 1 (b) but substituting cis-4-methyl-5-phenyl-4,5-dihydro-2-oxazolamine in place of 4-(4-fluorophenyl)-4,5-dihydro-2-oxazolamine, then cis-2,3,6,7-tetrahydro-6-methyl-7-phenyl-2-thioxo-4H-oxazolo[3,2,-a]-1,3,5-triazin-4-one is formed.

EXAMPLE 4

(Trans)-2,3,6,7-tetrahydro-6-methyl-7-phenyl-2-thioxo-4H-oxazolo[3,2,-a]-1,3,5-triazin-4-one (a)

Trans-4-methyl-5-phenyl-4,5-dihydro-2-oxazolamine

By following the procedure of Example 2 (a) but substituting threo amino-alcohol dl-norpseudoephedrine for α-aminomethyl benzyl alcohol, then trans-4-methyl-5-phenyl-4,5-dihydro-2-oxazolamine is formed.

(b)

(Trans)-2,3-6,7-Tetrahydro-6-methyl-7-phenyl-2-thioxo-4H-oxazolo[3,2-a]-1,3,5-triazin-4-one By following the procedure of Example 1 (b) but substituting trans-4-methyl-5-phenyl-4,5-dihydro-2-oxazolamine in place of 4-(4-fluorophenyl)-4,5-dihydro-2-oxazolamine, then trans-2,3-6-7-tetrahydro-6-methyl-7-phenyl-2-thioxo-4H-oxazolo[3,2-a]-1,3,5-triazin-4-one is formed.

EXAMPLE 5

(cis)-2,3,6,7-Tetrahydro-7-methyl-6-phenyl-2-thioxo-4H-oxazolo[3,2-a]-1,3,5-triazin-4-one (a) 5-Methyl-4-phenyl-4,5-dihydro-2-oxazolamine By following the procedure of Example 2 (a) but substituting β-amino-α-methylphenethyl alcohol for α-aminoethylbenzyl alcohol then 5-methyl-4-phenyl-4,5-dihydro-2-oxazolamine is formed.

(b)

(cis)-2,3,6,7-Tetrahydro-7-methyl-6-phenyl-2-thioxo-4H-oxazolo[3,2,-a]-1,3,5-triazin-4-one By following the procedure of Example 1 (b) but substituting 5-methyl-4-phenyl-4,5-dihydro-2-oxazolamine in place of 4-(4-fluorophenyl)-4,5-dihydro-2-oxazolamine then (cis)-2,3,6,7-tetrahydro-7-methyl-6-phenyl-2-thioxo-4H-oxazolo[3,2,-a]-1,3,5-triazin-4-one is formed.

EXAMPLES 6–21

By following the procedure of Example 1(b) but substituting a compound of Column I in place of 4-(4-fluorophenyl)-4,5-dihydro-2-oxazolamine, then a compound of Column II is formed. [The compounds of Column I are known; see G. I. Poos, et al., J. Med. Chem. 6 266 (1963) at page 267 for Examples 6–21.]

Column I

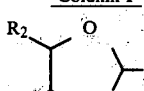

Column II

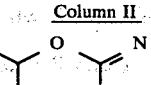

| Example | $R_1$ | $R_2$ |
|---|---|---|
| 6 | —H | Cl-phenyl |
| 7 | —H | 3-Cl-phenyl |
| 8 | —H | 4-Cl-phenyl |
| 9 | —H | 2,6-diCl-phenyl |
| 10 | —H | 4-Br-phenyl |
| 11 | —H | 4-F-phenyl |
| 12 | —H | 4-CF$_3$-phenyl |
| 13 | —H | 2-CF$_3$-phenyl |
| 14 | —H | 4-CH(CH$_3$)$_2$-phenyl |
| 15 | —H | 4-OCH$_3$-phenyl |
| 16 | —H | 4-(CH$_2$O-phenyl)-phenyl |
| 17 | —H | 3,4-diOCH$_3$-phenyl |
| 18 | —H | 3,4-(O-CH$_2$-O)-phenyl |
| 19 | —H | 3,4-diOCH$_3$-phenyl (with OCH$_3$) |
| 20 | —H | 4-(C(O)OCH$_3$)-phenyl |
| 21 | —CH$_3$ | F-phenyl |

EXAMPLES 22–30

By following the procedure of Example 2 (a) but substituting a compound of Column I in place of α-aminomethylbenzyl alcohol a compound of Column II is formed. Then by following the procedure of Example 1 (b) but substituting the compounds of Column II in place of 4-(4-fluorophenyl)-4,5-dihydro-2-oxazolamine then the product of Column III is formed.

Column I

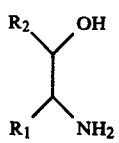

Column II

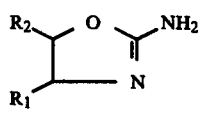

Column III

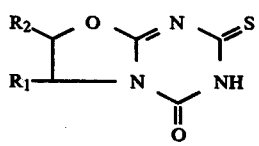

| Example | R₁ | R₂ |
|---|---|---|
| 22 | —⟨O⟩ | —H |
| 23 | —⟨O⟩—Cl | —CH₃ |
| 24 | —⟨O⟩ (Cl ortho) | —CH₃ |
| 25 | —⟨O⟩—Br | —H |
| 26 | —⟨O⟩—CF₃ | —H |
| 27 | —⟨O⟩—OCH₃ | —CH₃ |

-continued

Column I

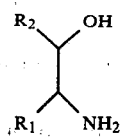

Column II

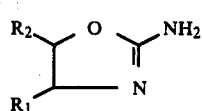

Column III

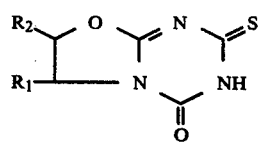

| Example | R₁ | R₂ |
|---|---|---|
| 28 | —⟨O⟩—OCH₃ | —H |
| 29 | —⟨O⟩—OCH₃ | —C₂H₅ |
| 30 | —⟨O⟩(OCH₃, OCH₃) | —H |

I claim:

1. A compound of the formula

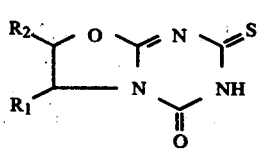

wherein
R₁ is phenyl or phenyl substituted with halogen, lower alkyl, phenyl lower alkyl, lower alkoxy, phenyl lower alkoxy, lower alkylthio, phenyl lower alkylthio, or halo lower alkyl when R₂ is hydrogen or lower alkyl; and R₂ is phenyl or phenyl substituted with halogen, lower alkyl, phenyl lower alkyl, lower alkoxy, phenyl lower alkoxy, lower alkylthio, phenyl lower alkylthio, or halo lower alkyl when R₁ is hydrogen or lower alkyl.

2. The compound of claim 1 wherein R₁ is phenyl substituted as defined above.

3. The compound of claim 1 wherein R₂ is phenyl substituted as defined above.

4. The compound of claim 2 wherein R₁ is a halo substituted phenyl.

5. The compound of claim 3 wherein R₂ is a halo substituted phenyl.

6. The compound of claim 4 wherein R₁ is a fluoro substituted phenyl.

7. The compound of claim 5 wherein R₂ is a fluoro substituted phenyl.

8. The compound of claim 4, 6-(4-fluorophenyl)-2,3,6,7-tetrahydro-2-thioxo-4H-oxazolo[3,2-a]-1,3,5-triazin-4-one.

* * * * *

UNITED STATES PATENT AND TRADEMARK OFFICE
CERTIFICATE OF CORRECTION

PATENT NO. : 4,311,840
DATED : January 19, 1982
INVENTOR(S) : Michael E. Condon

It is certified that error appears in the above-identified patent and that said Letters Patent are hereby corrected as shown below:

Column 4, line 8, "mlethoxycar" should read --ml ethoxycar--.
Column 4, line 28, "60-aminometh" should read
   --α-aminometh--.

Signed and Sealed this

Fifteenth Day of June 1982

[SEAL]

Attest:

GERALD J. MOSSINGHOFF

Attesting Officer

Commissioner of Patents and Trademarks